United States Patent
Glaser et al.

(10) Patent No.: US 12,337,087 B2
(45) Date of Patent: Jun. 24, 2025

(54) APPARATUS AND METHOD FOR DISINFECTING A HYDRAULIC CIRCUIT

(71) Applicant: FRESENIUS MEDICAL CARE DEUTSCHLAND GMBH, Bad Homburg (DE)

(72) Inventors: Benedict Glaser, Schweinfurt (DE); Steffen Interwies, Schweinfurt (DE); Matthias Brandl, Bad Koenigshofen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 237 days.

(21) Appl. No.: 15/742,615

(22) PCT Filed: Jul. 6, 2016

(86) PCT No.: PCT/EP2016/001163
§ 371 (c)(1),
(2) Date: Jan. 8, 2018

(87) PCT Pub. No.: WO2017/005366
PCT Pub. Date: Jan. 12, 2017

(65) Prior Publication Data
US 2018/0214621 A1    Aug. 2, 2018

(30) Foreign Application Priority Data
Jul. 7, 2015   (DE) .................. 10 2015 008 783.5

(51) Int. Cl.
*A61M 1/16*     (2006.01)
*A61L 2/18*     (2006.01)
*A61M 39/22*    (2006.01)

(52) U.S. Cl.
CPC .............. *A61M 1/169* (2013.01); *A61L 2/18* (2013.01); *A61M 39/227* (2013.01)

(58) Field of Classification Search
None
See application file for complete search history.

(56) References Cited

U.S. PATENT DOCUMENTS 5,244,568 A * 9/1993 Lindsay ................ A61M 1/168
                                                     210/87
5,591,344 A * 1/1997 Kenley ............... A61M 1/3647
                                                    210/764

(Continued)

FOREIGN PATENT DOCUMENTS

CN     104740707     7/2015
DE     102010011465  9/2011

(Continued)

*Primary Examiner* — Jason M Greene
*Assistant Examiner* — Eric J McCullough
(74) *Attorney, Agent, or Firm* — Kilyk & Bowersox, P.L.L.C.

(57) ABSTRACT

An apparatus for disinfecting a hydraulic circuit of a device for processing liquids for dialysis is provided. The apparatus includes at least one valve arrangement; at least one source for disinfectant; at least one first line which is connected or connectable to the source for disinfectant and to the hydraulic circuit; and at least one second line which branches off from the first line and is connected to environmental air or to an air reservoir. The valve arrangement has at least one first valve and at least one second valve which are located in the first line in front of and behind the point of the branching off of the second line from the first line. Furthermore, the valve arrangement has at least one third valve which is located in the second line, with the first and second lines being arranged such that, with opened first and third valves, the second line and the first line are ventilated between the (Continued)

second valve and the source so that the disinfectant contained therein runs off toward the source.

9 Claims, 1 Drawing Sheet

(56) References Cited

U.S. PATENT DOCUMENTS

2014/0190886 A1* 7/2014 Pudil .................. A61M 1/3406
                                                                       210/93
2014/0217020 A1* 8/2014 Meyer ................ A61M 1/3627
                                                                       96/182

FOREIGN PATENT DOCUMENTS

| EP | 1514563 | 3/2005 |
|----|---------|--------|
| WO | WO 2008/104367 | 9/2008 |
| WO | WO 2015/101508 | 7/2015 |

* cited by examiner

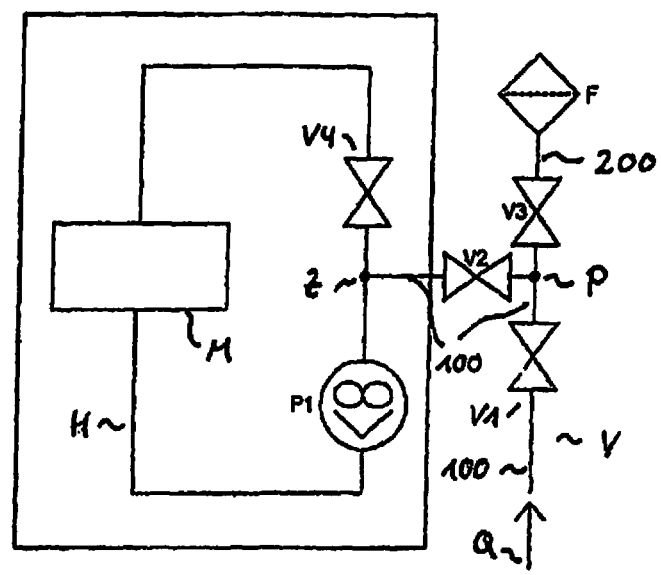

APPARATUS AND METHOD FOR DISINFECTING A HYDRAULIC CIRCUIT

BACKGROUND OF THE INVENTION

1. FIELD OF THE INVENTION

The present invention relates to an apparatus for disinfecting a hydraulic circuit of a device for processing liquids for dialysis comprising a valve arrangement.

2. DESCRIPTION OF THE RELATED ART

Such an apparatus is known from the prior art. The apparatus can be used in this respect to disinfect the hydraulic circuit of, for example, a water removal station which serves the provision of treated water purified after reverse osmosis operation. This filling station can output the required quantity of purified water to a mobile tank.

A filling station is known from DE 10 2010 011 465 A1 which serves the output of dialysis liquid to a mobile tank. This tank is traveled to the treatment station and is then connected to the dialysis device. This dialysis device draws the dialysis liquid required for the treatment from the mobile tank.

A mobile arrangement is known from WO 2008/104367 A2 which serves the preparation of the ready-to-use dialysis solution.

Hydraulic circuits of dialysis devices or of other components such as the above-named filling station have to be regularly disinfected. This takes place, for example, in that a generally liquid disinfectant is drawn into the hydraulic circuit by vacuum generation in the hydraulic circuit.

To be able to automate this process and not to have to connect the disinfectant to the hydraulic circuit again for each disinfection, it is necessary to connect a larger quantity of disinfectant in a container directly to the device hydraulics or to the hydraulic circuit. It is known, for example, to connect a canister having a filling volume of 5 to 10 l of liquid disinfectant to the hydraulic circuit.

The advantage of a simple handling is admittedly associated with this, but there is a disadvantage in that with a vacuum in the hydraulic circuit disinfectant can enter into the hydraulic circuit due to a leak at a valve which separates the hydraulic circuit from the source for the disinfectant or due to an incorrect valve control, which may result in injury to the patient under certain circumstances.

There is a further disadvantage in that the disinfectant can crystallize in the intake hose or in the valves since there can generally be several days to weeks between the individual disinfection cycles. Such a crystallization can result in a disturbance or in a failure of the respective component such as an incorrectly closing valve.

To prevent the unwanted suction of disinfectant into the hydraulic circuit with a high probability, two valves connected in series are used in known devices. It is furthermore known only to use one valve, but to subject it to a regular leak test, which is associated with an additional effort.

A disinfecting method is known from EP 0 436 855 A1 in which the dialysis device is connected via stub lines to a fresh water inflow line, which can be shut off, on the one hand, and to a water outflow line, which can be shut off, on the other hand. A connection line, which can be shut off by a valve, is located between these lines. In a first step, the dialysis device is flushed with fresh water with a closed valve of the connection line and, in a second step, heated water circulates with an open valve and a shut off fresh water inflow line and a shut off water outflow line.

EP 1 514 563 A1 describes an arrangement for disinfecting a dialysis device in which a reception space is arranged between the source for the disinfectant and the hydraulic circuit of the dialysis device. It is prevented by a siphon-like connection of the reception space to the source for the disinfectant that, e.g. with a defective valve, liquid enters from the dialyzate circuit into the source for the disinfectant.

SUMMARY OF THE INVENTION

It is the underlying object of the present invention to further develop a disinfecting method and an apparatus for disinfecting such that it can be prevented with a comparatively small effort that disinfectant enters accidentally into the hydraulic circuit of the device, such as a filling station or a dialysis device.

This object is achieved by an apparatus having the features to be more fully defined hereinafter.

Provision is accordingly made that the apparatus comprises the following:
- at least one valve arrangement;
- at least one source for disinfectant;
- at least one first line which is connected or connectable to the source for disinfectant and to the hydraulic circuit;
- at least one second line which branches off from the first line and is connected to environmental air or to an air reservoir;
- wherein the valve arrangement has at least one first valve and at least one second valve which are located in the first line in front of and behind the point of the branching off of the second line from the first line; and wherein the valve arrangement furthermore has at least one third valve which is located in the second line,
- with the first and second lines being arranged such that, with opened first and third valves, the second line and the first line are ventilated between the second valve and the source so that the disinfectant contained therein runs off toward the source.

It is ensured by this apparatus that, with a closed second valve, i.e. on a separation of the apparatus in accordance with the invention from the hydraulic circuit of the device, no disinfectant enters into the hydraulic circuit even when the second valve does not close tightly or is accidentally open. This is prevented in that the first and second lines are arranged such that the disinfectant runs back to the source with a closed second valve and does not remain in the first and second lines if no disinfection is being carried out.

If the second valve does not close tightly or if it is accidentally open, with a vacuum present in the hydraulic circuit which is preferably generated by a pump located therein, air is drawn into the hydraulic circuit and not disinfectant. An unintentional application of disinfectant is thus reliably prevented.

No serial connection of two shut-off valves which separate the apparatus from the device is necessary for this purpose, whereby a corresponding apparatus simplification results.

It is pointed out at this point that the term "air" includes any desired gas or gas mixture. The term the "source" for the disinfectant includes any desired unit by means of which disinfectant can be provided such as a container, a bag or a line, etc.

A control and regulation unit is preferably present which is configured such that it operates the valve arrangement in at least one first operating mode in which no disinfectant is supplied to the hydraulic circuit and in at least one second operating mode in which disinfectant is supplied to the hydraulic circuit, wherein the second valve and preferably also the first valve are closed and the third valve is open in the first operating mode and wherein the first and second valves are open and the third valve is closed in the second operating mode.

The control or regulation unit is preferably configured such that it operates the valve arrangement at the end of the second operating mode, i.e. after the supply of disinfectant to the hydraulic circuit, such that first the second valve is closed and the third valve is opened and such that the first valve is subsequently closed.

The present invention relates to the apparatus for disinfecting a device having a hydraulic circuit as such and also to the combination of the apparatus with such a device, i.e. e.g. the combination of the apparatus with a filling station or with a dialysis device.

The apparatus can be fixedly or releasably connected to the device.

At least one pump for generating a vacuum in the hydraulic circuit is preferably located in the hydraulic circuit of the device, with the first line opening into the hydraulic circuit on the suction side of the pump. This pump is e.g. used for the recirculation of a dialysis liquid or also of the disinfectant.

At least one fourth valve is preferably located in the hydraulic circuit and is arranged upstream of the opening of the first line into the hydraulic circuit in the direction of flow of the liquid in the hydraulic circuit. The first line preferably opens in the hydraulic circuit between this fourth valve and the pump of the hydraulic circuit.

The control or regulation unit can be configured such that it has the effect in the first operating mode (i.e. when no disinfectant is supplied) that the fourth valve is open and has the effect in the second operating mode (i.e. when disinfectant is supplied) that the fourth valve is closed.

The valves are preferably open/closed valves which can be in exactly two positions, i.e. in the closed position and in the open position. However, the case is also covered by the invention that the valves are butterfly valves whose flow cross-section is e.g. continuously variable between the open and closed positions.

The valves can be valves to be actuated manually, but it is preferred if they are also valves which are provided with a drive which can be controlled by a control or regulation unit.

The first, second and third valves are preferably electrically operated valves.

The first and second valves are preferably closed without current and the third valve is open without current.

The hydraulic circuit can be a hydraulic circuit of a filling station for the filling of a container or of a dialysis device with dialysis liquid, RO water or another liquid or it can be a hydraulic circuit of a dialysis device or of another device for blood treatment.

The present invention furthermore relates to a method for disinfecting a hydraulic circuit of a device for processing liquids for dialysis, wherein no disinfectant is supplied to the hydraulic circuit in a first operating mode and wherein disinfectant is supplied to the hydraulic circuit in a second operating mode, wherein at least one apparatus is used for disinfecting the hydraulic circuit which has at least one source for the disinfectant and which has at least one first line which extends from the source for the disinfectant to the hydraulic circuit and in which at least one valve for shutting off the first line is located, wherein the first line is closed in the first operating mode and is ventilated between the valve and the source and wherein the first line is open and is not ventilated in the second operating mode.

The method is preferably carried out using an apparatus in accordance with at least one of the configurations as just described in the summary of the invention set forth above.

It is conceivable that, in the second operating mode, a vacuum is generated at that point in the hydraulic circuit at which the first line opens into the hydraulic circuit Provision can furthermore be made that the hydraulic circuit is operated such that, in the second operating mode, a valve is closed which is located upstream of that point in the hydraulic circuit at which the first line opens into the hydraulic circuit. In a further preferred embodiment, a pump for generating a vacuum in the region of the opening is located downstream of this opening.

BRIEF DESCRIPTION OF THE DRAWING

Further details and advantages of the invention will be explained in more detail with reference to an embodiment shown in the drawing.

The only FIGURE shows a device having a hydraulic circuit and the apparatus connected thereto for its disinfection.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The reference symbol H shows the hydraulic system or the hydraulic circuit of a filling station.

The pump P1 and a valve V4, which is called a fourth valve within the framework of the invention, are located in the hydraulic circuit H.

A mixing vessel M in which different components required for the preparation of a dialysis solution are mixed is furthermore located in the hydraulic circuit H. This mixture is recirculated by means of the pump P1. If the dialysis liquid is, for example, to be output to a mobile tank or to a dialysis device, this is done via an outflow line, not shown.

To be able to disinfect the hydraulic circuit H, the apparatus V is provided which has a source Q for the disinfectant and a valve arrangement comprising the first valve V1, the second valve V2 and the third valve V3.

The reference numeral 100 designates a first line which extends from the source Q to the hydraulic circuit H and opens into it at the point Z.

A second line 200 whose other end is connected to the environmental atmosphere branches off from the first line 100 at the point P between the first valve V1 and the second valve V2. A filter F which prevents the penetration of contaminants from the environment into the second line 200 is located in the end region of the second line 200.

The valves V1, V2 and V4 are normal shut-off valves which are closed without current. The valve V3 is a hose pinch valve which is open without current.

The dead space between the valves V1, V2 and V3 should be kept very small. This applies accordingly to the line piece between the valve V2 and the stretch between V4 and the pump P1.

In normal operation, i.e. in the first operating mode in accordance with the invention in which no disinfectant is supplied to the hydraulic circuit H, the valves V1, V2 and V3 are without current, i.e. V1 and V2 are closed and V3 is open. The line 200 and the section of the first line 100 from V2 to the source Q are ventilated, i.e. are connected to the environmental atmosphere.

If disinfectant is to be sucked in (second operating mode in accordance with the invention), V4 is closed, V2 and V1 are open and V3 is closed. The line system of the apparatus V is thus cut off from the environmental atmosphere and disinfectant is sucked from the source Q into the hydraulic circuit H by the vacuum which is generated by the running pump P1.

After the suction of disinfectant has taken place, first V2 is closed and V3 is opened. This has the result that the remaining disinfectant which is located in the second line 200 and in the section of the first line 100 between the valve V2 and the source Q flows back to the source. These line sections are then air-filled. This flowing back takes place due to gravity.

The valve V1 is subsequently closed.

It is ensured by the hydrostatic arrangement of the lines 100 and 200 and of the valves V1, V2 and V3 that the suction stretch between the first valve V1 and the source Q runs completely empty. This applies accordingly to the line piece from the second valve V2 up to the first valve V1.

It is thus ensured that, after the end of the disinfection procedure or in normal operation of the device, air and not disinfectant is applied to the valve V2 at the side remote from the hydraulic circuit.

If the valve V2 is incorrectly controlled, e.g. if it is open or does not close tightly during the treatment or during the preparation of dialysis liquid, air is sucked in via the valve V3.

An accidental penetration of disinfectant into the hydraulic circuit H can thus be prevented. A valve arrangement having two valves connected in series such as two valves V3 connected in series is not necessary and is preferably not provided between the apparatus and the hydraulic circuit.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A system comprising an apparatus for disinfecting a hydraulic circuit, and a device for processing liquids for dialysis, wherein
the system comprises a valve arrangement,
the apparatus comprises at least one first valve, at least one second valve, and at least one third valve that are parts of the valve arrangement,
the device for processing liquids for dialysis comprises a recirculating hydraulic circuit, a pump, and a fourth valve that is part of the valve arrangement, the pump and the fourth valve being arranged in the recirculating hydraulic circuit,
the at least one second valve and the fourth valve are separate from and operate independently of one another,
the at least one first valve, the at least one second valve, and the fourth valve are electrically operated shut-off valves that are closed in the absence of an electrical current,
the at least one third valve is electrically operated and is open in the absence of an electrical current;
the system further comprises
a source of disinfectant, containing disinfectant,
a first line that is connected to both the source of disinfectant and to the recirculating hydraulic circuit,
a second line that branches off of the first line at a point and that is connected to environmental air or to an air reservoir, and
a control and regulation unit, and further wherein
the pump is configured for generating a vacuum in the recirculating hydraulic circuit,
the first line opens into the recirculating hydraulic circuit at an opening on a suction side of the pump,
the at least one first valve and the at least one second valve are located in the first line,
the point of branching off of the second line from the first line is between the at least one first valve and the at least one second valve,
the at least one third valve is located in the second line,
the fourth valve is arranged upstream of the opening with respect to a direction of flow of liquid in the recirculating hydraulic circuit;
the first line and the second line are arranged such that, when the at least one first valve and the at least one third valve are open, the second line and the first line are ventilated between the at least one second valve and the source of disinfectant so that the disinfectant contained in the second line and in the first line between the at least one second valve and the source of disinfectant, flows back to the source of disinfectant;
the control and regulation unit is configured to operate the valve arrangement in a first operating mode in which no disinfectant is supplied to the recirculating hydraulic circuit, and in a second operating mode in which disinfectant is supplied to the recirculating hydraulic circuit,
the at least one first valve and the at least one second valve are closed and the at least one third valve is open, in the first operating mode,
the source of disinfectant is connected to the recirculating hydraulic circuit via the first line, via the at least one first valve, and via the at least one second valve, in the first operating mode,
the at least one first valve and the at least one second valve are open and the at least one third valve is closed, in the second operating mode, and
the control and regulation unit is further configured to operate the valve arrangement after supplying disinfectant to the hydraulic circuit and completing the second operating mode, such that the at least one first valve and the at least one second valve are closed, the at least one third valve is opened, and, subsequently, the at least one first valve is closed.

2. The system in accordance with claim 1, wherein the control and regulation unit is configured to operate in the first operating mode such that the fourth valve is open and to operate in the second operating mode such that the fourth valve is closed.

3. The system in accordance with claim 1, wherein the recirculating hydraulic circuit is: a hydraulic circuit of a filling station for the filling of a container; or a hydraulic circuit of a filling station of a dialysis device; or is or a hydraulic circuit of a dialysis device.

4. A method for disinfecting a recirculating hydraulic circuit of a device for processing liquids for dialysis, the method comprising:

connecting an apparatus to the recirculating hydraulic circuit, wherein the apparatus comprises a valve arrangement, a source of disinfectant which source contains disinfectant, a first line that is connected to the source of disinfectant and to the recirculating hydraulic circuit, at least one second line which branches off of the first line at a point and that is connected to environmental air or to an air reservoir, and at least one control and regulation unit, the device for processing liquids for dialysis comprises at least one pump located in the recirculating hydraulic circuit, the pump being configured for generating a vacuum in the recirculating hydraulic circuit, the at least one first line opening into the recirculating hydraulic circuit at a suction side of the pump, the valve arrangement comprises a first valve and a second valve, that are located in the first line, the point of branching off of the at least one second line from the at least one first line is between the first valve and the second valve, the valve arrangement further comprises a third valve that is arranged in the at least one second line, the device for processing liquids for dialysis comprises a fourth valve arranged in the recirculating hydraulic circuit and arranged upstream of a point at which the at least one first line opens into the recirculating hydraulic circuit, with respect to a direction of flow of liquid in the recirculating hydraulic circuit, the second valve and the fourth valve are separate from and operate independently of one another, each of the first, second, and fourth valves is an electrically operated shut-off valve that is closed without electrical current, and the third valve is electrically operated and open without current;

and the method further comprises operating, with the at least one control and regulation unit, the valve arrangement and the fourth valve in a first operating mode in which the first and second valves are closed, the third valve is open, and no disinfectant is supplied to the recirculating hydraulic circuit, operating, with the at least one control and regulation unit, the valve arrangement and the fourth valve in a second operating mode in which the first and second valves are open, the third valve is closed, and disinfectant is supplied to the recirculating hydraulic circuit; wherein the first line is closed by said at least one second valve (V2) in the first operating mode and is ventilated between the at least one second valve (V2) and the source, wherein the source of disinfectant is connected to the hydraulic circuit via the first line and the at least one first valve (V1) and the at least one second valve (V2) in the first operating mode, and wherein the first line is open and is not ventilated in the second operating mode;

the first line and the second line being arranged such that, when the first valve (V1) and the third valve (V3) are opened, the second line and the first line are ventilated between the second valve (V2) and the source so that the disinfectant contained therein runs off toward the source; and operating, with the control and regulation unit, the valve arrangement and the fourth valve, after the supply of disinfectant to the recirculating hydraulic circuit and completion of the second operating mode, to close the first the second valves, open the third valve, and, subsequently closing the first valve.

5. The method as set forth in claim 4, wherein, in the second operating mode, the control and regulation unit closes the fourth valve and the pump generates a vacuum at the point in the recirculating hydraulic circuit where the first line opens into the hydraulic circuit.

6. The method as set forth in claim 5, wherein, in the first operating mode, the control and regulation unit opens the fourth valve.

7. The system in accordance with claim 1, further comprising a filter along the second line for preventing penetration of contaminants from the environment into the second line.

8. The method in accordance with claim 4, wherein the apparatus further comprises a filter along the second line for preventing penetration of contaminants from the environment into the second line, and the method further comprises filtering air, with the filter, as air enters the second line and the first line when the second line and the first line are ventilated.

9. The system of claim 1, wherein the at least one third valve is a hose pinch valve.

* * * * *